United States Patent
Candau

(12) 
(10) Patent No.: US 6,296,835 B1
(45) Date of Patent: Oct. 2, 2001

(54) PHOTOPROTECTIVE/COSMETIC COMPOSITIONS COMPRISING BIS-HYDROXYPHENYLBENZOTRIAZOLE AND BENZAZOLYL/BENZODIAZOLYL SUNSCREENS

(75) Inventor: Didier Candau, Bievres (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 09/589,116

(22) Filed: Jun. 8, 2000

(30) Foreign Application Priority Data

Jun. 8, 1999 (FR) .................................................. 99 07205

(51) Int. Cl.[7] .............................. A61K 7/42; A61K 7/44; A61K 7/00
(52) U.S. Cl. .............................. 424/59; 424/60; 424/400; 424/401
(58) Field of Search ................................ 424/59, 60, 400, 424/401

(56) References Cited

FOREIGN PATENT DOCUMENTS 0893119    1/1999   (EP) .

*Primary Examiner*—Shelley A. Dodson
(74) *Attorney, Agent, or Firm*—Burns, Doane, Swecker & Mathis, L.L.P.

(57) ABSTRACT

Topically applicable sunscreen/cosmetic compositions well suited for the SPF synergistically enhanced photoprotection of human skin and/or hair against the damaging effects of UV-irradiation, particularly solar radiation, comprise synergistically UV-photoprotecting effective amounts of each of (a) at least one bis-hydroxyphenylbenzotriazole sunscreen compound and (b) at least one second sunscreen compound which comprises at least two benzazolyl functional groups per molecule and/or at least one sunscreen compound which comprises at least one benzodiazolyl functional group per molecule, formulated into a topically applicable, cosmetically acceptable vehicle, diluent or carrier therefor, advantageously formulated as an oil-in-water emulsion.

41 Claims, No Drawings

PHOTOPROTECTIVE/COSMETIC COMPOSITIONS COMPRISING BIS-HYDROXYPHENYLBENZOTRIAZOLE AND BENZAZOLYL/BENZODIAZOLYL SUNSCREENS

CROSS-REFERENCE TO PRIORITY APPLICATION

This application claims priority under 35 U.S.C. §119 of FR-99/07205, filed Jun. 8, 1999, hereby expressly incorporated by reference.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen" or "antisun" compositions), and to the use of same for the cosmetic applications indicated above.

This invention more especially relates to the aforesaid sunscreen/antisun compositions comprising, in a cosmetically acceptable support (vehicle, diluent or carrier) unique immixture of (a) at least one bis-hydroxyphenylbenzotriazole compound as a first screening agent and (b) as a second screening agent, at least one compound comprising at least two benzazolyl functional groups or at least one compound comprising at least one benzodiazolyl functional group. This admixture imparts enhanced sun protection factors to the subject compositions via an unexpected synergistic effect.

2. Description of the Prior Art

It is known to this art that light radiation with wavelengths from 280 nm to 400 nm promotes tanning of the human epidermis and that irradiation of wavelengths of from 280 nm to 320 nm, i.e., UV-B irradiation, causes skin burns and erythema which may be harmful to the development of a natural tan; this UV-B radiation should thus be screened from the skin.

It is also known to this art that UV-A radiation, of wavelengths from 320 to 400 nm, which tans the skin, also adversely affects it, in particular in the case of sensitive skin or of skin which is continually exposed to solar radiation. In particular, UV-A rays cause a loss of elasticity of the skin and the appearance of wrinkles, promoting a premature aging thereof. Such irradiation promotes triggering of the erythemal reaction or amplifies this reaction in certain individuals and may even be the cause of phototoxic or photoallergic reactions. It is thus desirable to also screen out UV-A radiation.

A wide variety of cosmetic compositions for the photoprotection of human skin (against UV-A and/or UV-B) are known to this art.

These sunscreen/antisun compositions are typically in the form of an emulsion of oil-in-water type (i.e., a cosmetically acceptable support comprising an aqueous dispersing continuous phase and an oily dispersed discontinuous phase) which contains, in varying concentrations, one or more conventional lipophilic and/or hydrophilic organic sunscreens capable of selectively absorbing the harmful or deleterious UV radiation, these screening agents (and the amounts thereof) being selected as a function of the desired protection factor (the protection factor (PF) being expressed mathematically by the ratio of the irradiation time required to reach the erythema-forming threshold with the UV screening agent, to the time required to attain the erythema-forming threshold without a UV screening agent).

SUMMARY OF THE INVENTION

It has now surprisingly and unexpectedly been determined that unique intimate admixture, in proportions within well defined limits, of two specific sunscreens per se known to this art provides, via notable synergistic effect, sunscreen/antisun compositions which have markedly improved sun protection factors that are in all instances very much higher than those which can be obtained from either of the screening agents administered alone.

Briefly, the present invention features novel cosmetic compositions, in particular sunscreen/antisun compositions, comprising, formulated into a topically applicable, cosmetically acceptable support therefor, (i) at least one bis-hydroxyphenylbenzotriazole hydrocarbon-based compound, as a first screening agent, and (ii) at least one compound comprising at least two benzazolyl functional groups per molecule and/or at least one compound comprising at least one benzodiazolyl functional group per molecule, as a second screening agent; the said first and second screening agents are present in the subject compositions in proportions which elicit synergistic activity in respect of the sun protection factors imparted.

The present invention also features the use of such compositions for the formulation of cosmetic compositions for protecting the skin and/or the hair against ultraviolet radiation, in particular solar radiation.

DETAILED DESCRIPTION OF BEST MODE AND SPECIFIC/PREFERRED EMBODIMENTS OF THE INVENTION

More particularly according to the present invention, by the expression "comprising at least two benzazolyl functional groups" is intended comprising at least two groups of benzoxazolyl, benzothiazolyl or benzimidazolyl type per molecule.

By the expression "comprising at least one benzodiazolyl functional group" is intended comprising one group of benzodioxazolyl, benzodithiazolyl or benzodiimidazolyl type per molecule.

Exemplary bis-hydroxyphenylbenzotriazole compounds according to the invention include the preferred compounds having the structural formula (1) below:

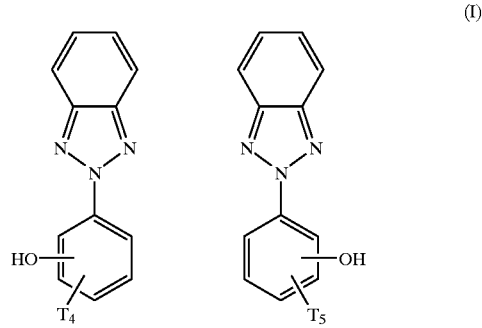

in which the radicals $T_4$ and $T_5$, which may be identical or different, are each a $C_1$–$C_{18}$ alkyl radical optionally substituted with one or more radicals selected from among $C_1$–$C_4$ alkyl, $C_5$–$C_{12}$ cycloalkyl or aryl radicals (such as phenyl or benzyl radicals). Preferably, $T_4$ and $T_5$ are simultaneously an α,α-dimethylbenzyl radical. These compounds are known per se and are described in GB-A-2,303,549, DE-197 26 184 and EP-A-893,119, hereby expressly incorporated by reference.

Other preferred bis-hydroxyphenylbenzotriazole compounds according to the invention include those particularly preferred compounds having the structural formula (II) below:

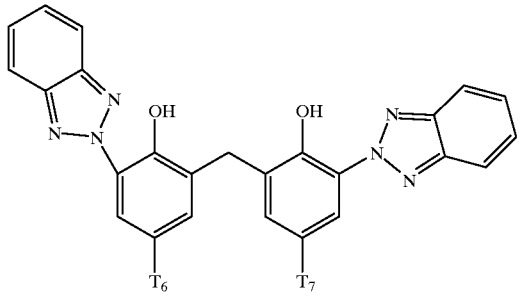

(II)

in which the radicals $T_6$ and $T_7$, which may be identical or different, are each a $C_1$–$C_{18}$ alkyl radical optionally substituted with one or more radicals selected from among $C_1$–$C_4$ alkyl, $C_5$–$C_{12}$ cycloalkyl or aryl radicals. These compounds are known per se and are described in the aforesaid GB-A-2,303,549, DE-197 26 184 and EP-A-893,119.

Among the compounds of formula (II), those more particularly preferred have the following structures:

Compound (a)

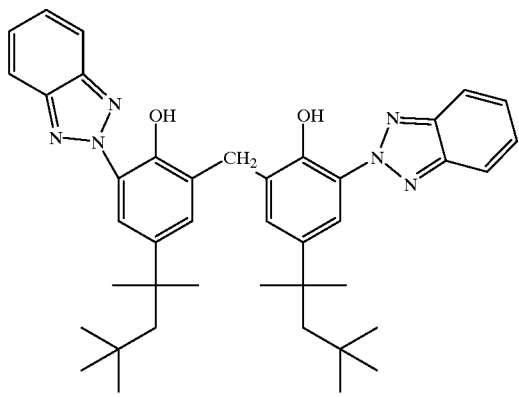

Compound (b)

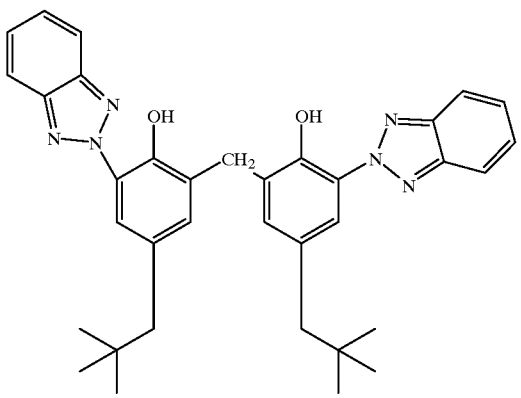

In the above formulae (I) and (II):
(i) the $C_1$–$C_{18}$ alkyl radicals may be linear or branched and include, for example, methyl, ethyl, n-propyl, isopropyl, n-butyl, isobutyl, tert-butyl, n-amyl, n-hexyl, n-heptyl, n-octyl, isooctyl, n-nonyl, n-decyl, n-undecyl, n-dodecyl, tetradecyl, hexadecyl and octadecyl radicals;
(ii) the $C_5$–$C_{12}$ cycloalkyl radicals include, for example, cyclopentyl, cyclohexyl and cyclooctyl radicals;
(iii) the aryl radicals include, for example, phenyl and benzyl radicals.

The screening agent(s) of the bis-hydroxyphenylbenzotriazole hydrocarbon-based compound type according to the invention are advantageously present in the subject screening compositions in a total concentration ranging from 0.1% to 15% by weight, approximately, and preferably from 0.2% to 10% by weight, approximately, relative to the total weight of the composition.

In one specific embodiment of the invention, the bis-hydroxyphenylbenzotriazole hydrocarbon-based derivatives may be in a specific form and may be insoluble or substantially insoluble in the usual cosmetic solvents (water, alcohols, fatty acids, etc.).

Consistent herewith, by the expression "insoluble or substantially insoluble compounds" are intended compounds whose solubility in water is less than 0. 1% by weight, whose solubility in liquid petroleum jelly is less than 1% by weight and, lastly, whose solubility in a mixture of triglyceride esters such as "Miglyol 812" marketed by Dynamit Nobel is less than 2%, also by weight.

The bis-hydroxyphenylbenzotriazole compounds can be converted to a particular suitable form by any means such as, in particular, dry-grinding or grinding in a solvent medium, screening, atomization, micronization or spraying.

In another specific embodiment of the invention, the bis-hydroxyphenylbenzotriazole compounds can be in insoluble micronized form. The average size of such particles will generally range from 0.01 to 2 μm, more preferably from 0.02 to 1.5 μm and more particularly from 0.05 to 1.0 μm.

The bis-hydroxyphenylbenzotriazole compounds in micronized form can be obtained by a process of grinding a hydroxyphenylbenzotriazole hydrocarbon-based derivative in the form of particles of coarse size in the presence of a suitable surfactant for improving the dispersion of the particles thus obtained in cosmetic formulations.

One example of a process for micronizing bis-hydroxyphenylbenzotriazole compounds is described in GB-A-2,303,549 and EP-A-893,119. The grinding apparatus according to these documents can be a jet mill, a bead mill, a vibration mill or a hammer mill and preferably a mill with high-speed stirring or an impact mill and more particularly a rotating-bead mill, a vibrating mill, a tube mill or a shaft mill.

According to this specific process, the surfactants used for grinding the said bis-hydroxyphenylbenzotriazole compounds are alkylpolyglucosides of structure $C_nH_{2n+1}O(C_6H_{10}O_5)_xH$ in which n is an integer ranging from 8 to 16 and x is the average degree of polymerization of the structural unit $(C_6H_{10}O_5)$ and ranges from 1.4 to 1.6. These can be selected from among $C_1$–$C_{12}$ esters of a compound of structure $C_nH_{2n+1}O(C_6H_{10}O_5)_xH$ and, more specifically, an ester obtained by reacting a $C_1$–$C_{12}$ carboxylic acid such as formic acid, acetic acid, propionic acid, butyric acid, sulfosuccinic acid, citric acid or tartaric acid with one or more free OH functions on the glucoside unit $(C_6H_{10}O_5)$. Said surfactants are advantageously used at a concentration ranging from 1% to 50% by weight and more preferably from 5% to 40% by weight relative to the bis-hydroxyphenylbenzotriazole hydrocarbon-based screening agent in its micronized state.

Exemplary compounds comprising at least two benzazolyl functional groups in accordance with the invention are those preferably having the structural formula (III) below:

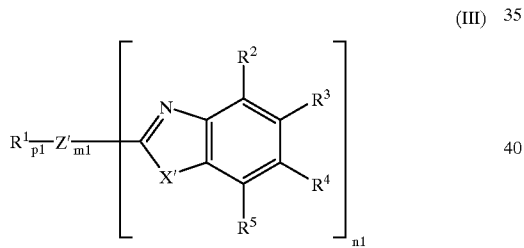

(III)

in which Z' is an organic residue of valency $(p_1+n_1)$ comprising one or more double bonds situated such that they complete the system of double bonds of at least two benzazolyl functional groups, which may be identical or different, as circumscribed within the brackets to constitute a totally conjugated moiety; X' is S, O or $NR^6$; $R^1$ is hydrogen, $C_1$–$C_{18}$ alkyl, $C_1$–$C_4$ alkoxy, $C_5$–$C_{15}$ aryl, $C_2$–$C_{18}$ acyloxy, $SO_3Y'$ or $COOY'$; the radicals $R^2$, $R^3$, $R^4$ and $R^5$, which may be identical or different, are each a nitro group or a radical $R^1$; $R^6$ is hydrogen, $C_1$–$C_4$ alkyl or $C_1$–$C_4$ hydroxyalkyl; Y' is hydrogen, Li, Na, K, $NH_4$, 1/2Ca, 1/2Mg, 1/3Al or a cation resulting from the neutralization of a free acid group with a nitrogenous organic base; $m_1$ is 0 or 1; $n_1$ is a number ranging from 2 to 6; and $p_1$ is a number ranging from 1 to 4; with the proviso that $p_1+n_1$ does not exceed the value 6.

The compounds of formula (III) in accordance with the invention are water-soluble UV-A screening agents that are described in EP-A-0,669,323. These are also described and prepared according to the syntheses indicated in U.S. Pat. No. 2,463,264 and in EP-A-0,669,323, also hereby incorporated by reference.

Among the compounds of formula (III) according to the invention which are preferred are those for which the group Z' is selected from among:

(a) an olefinic linear aliphatic $C_2$–$C_6$ hydrocarbon-based radical which can be interrupted with a $C_5$–$C_{12}$ aryl group or a $C_4$–$C_{10}$ heteroaryl group such as, for example:

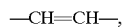

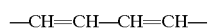

or

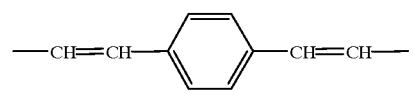

(b) a $C_5$–$C_{15}$ aryl radical which can be interrupted with an olefinic linear aliphatic $C_2$–$C_6$ hydrocarbon-based radical such as, for example, the following:

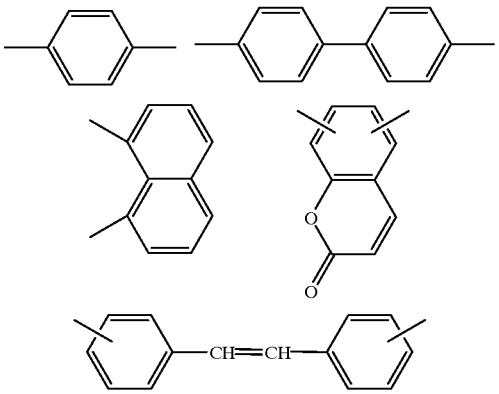

(c) a $C_3$–$C_{10}$ heteroaryl radical such as, for example, the following:

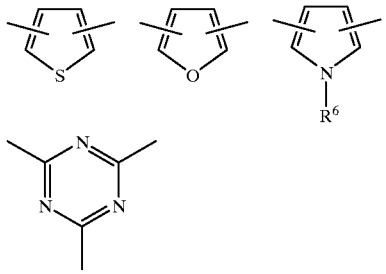

in which $R^6$ is as defined above; the said radicals Z' as defined in paragraphs (a), (b) and (c) optionally being substituted with $C_1C_{-6}$ alkyl, $C_1$–$C_6$ alkoxy, phenoxy, hydroxyl, methylenedioxy or amino radicals optionally substituted with one or two $C_1$–$C_5$ alkyl radicals.

Exemplary compounds of formula (III) are those having the structures below, as well as the salts thereof:

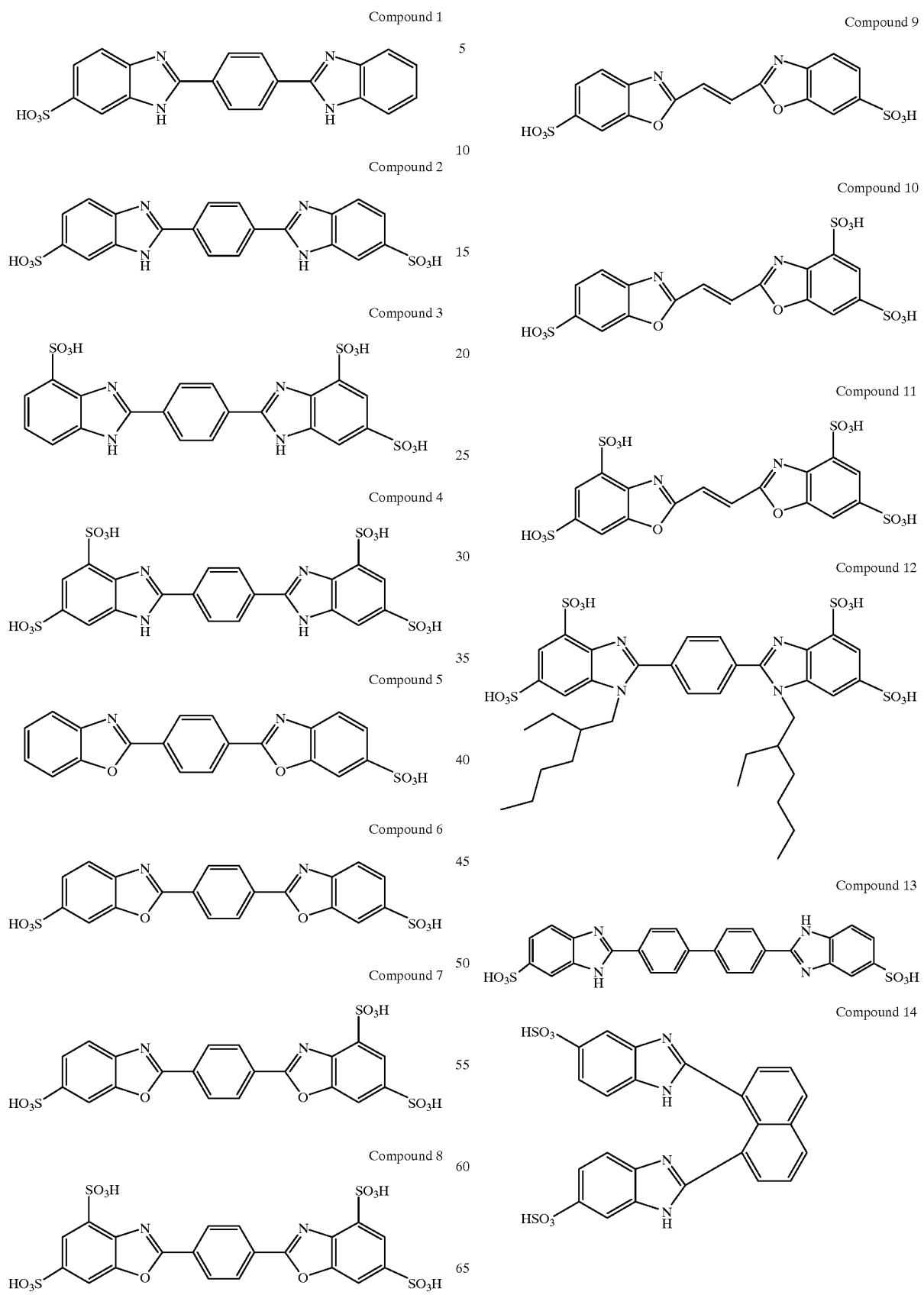

-continued
Compound 15
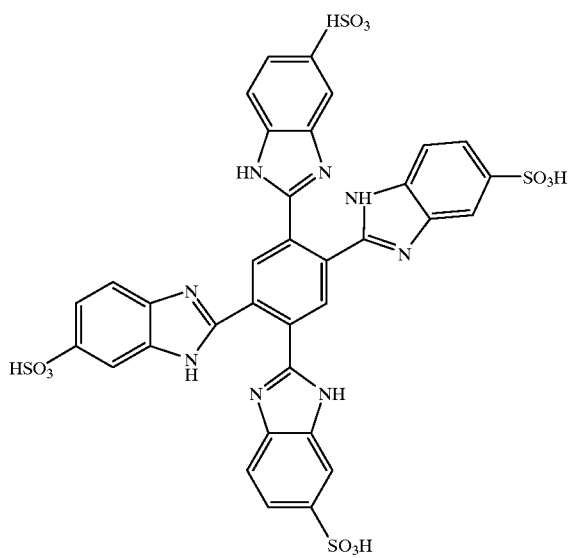
Compound 16
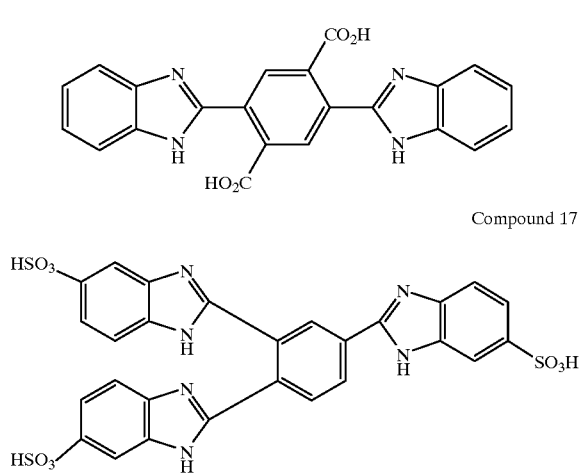
Compound 17
Compound 18
Compound 19
Compound 20
-continued
Compound 21
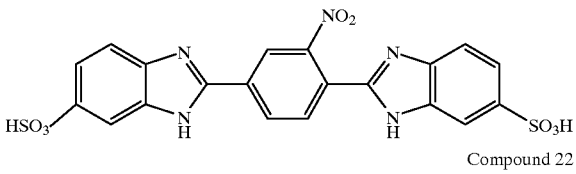
Compound 22
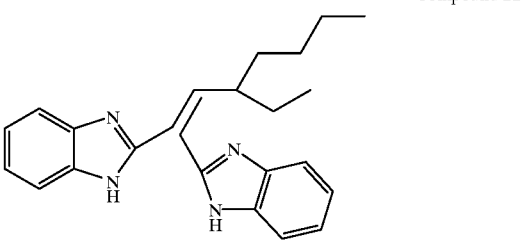
Compound 23
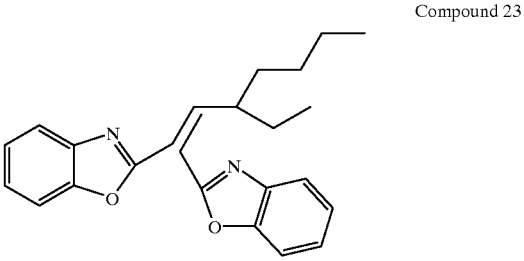
Compound 24
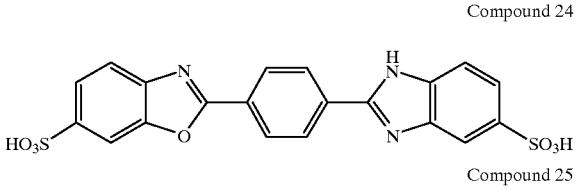
Compound 25
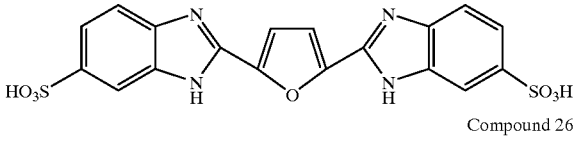
Compound 26
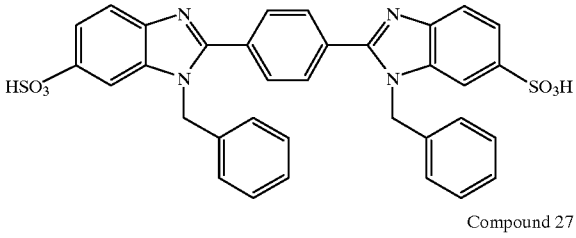
Compound 27
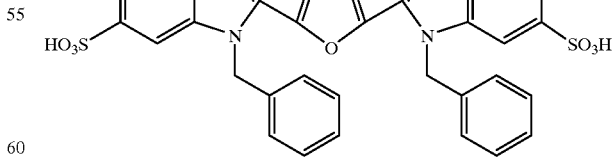
Among the aforesaid compounds, that most particularly preferred is 1,4-bis(benzimidazolyl)-phenylene-3,3',5,5'-tetrasulfonic acid (Compound 4), as well as the salts thereof, having the following structure:

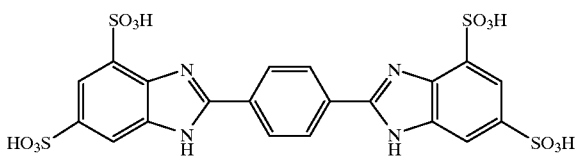

Other examples of compounds comprising at least two benzazolyl functional groups are the following compounds, as well as the salts thereof:

Compound 28

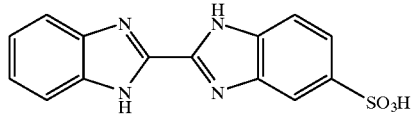

Compound 29

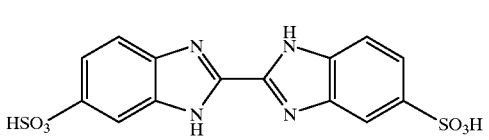

Compound 30

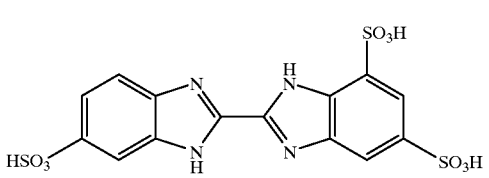

Compound 31

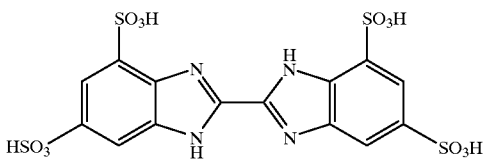

Exemplary compounds comprising at least one benzodiazolyl functional group according to the invention include, in particular, the following, as well as the salts thereof:

The compound(s) containing benzazolyl or benzodiazolyl functional groups in accordance with the invention are advantageously present in the subject compositions at a concentration of from 0.1% to 15%, preferably from 0.2% to 10%, by weight relative to the total weight of the composition.

As indicated above, it is a characteristic of the present invention that the two types of sunscreens are both present in the final composition in a respective proportion such that an appreciable synergistic effect is elicited as regards the sun protection factor imparted by the resulting combination.

In addition, and in general, it should be noted that the concentrations and ratios of bis-hydroxyphenylbenzotriazole compounds and of compounds containing benzazolyl or benzodiazolyl groups as defined above are selected such that the sun protection factor of the final composition is preferably at least 2.

In one preferred embodiment of the present invention, the cosmetically acceptable support in which the various sunscreens are formulated is an emulsion of oil-in-water type.

Of course, the sunscreen/antisun cosmetic compositions according to the invention can contain one or more additional hydrophilic or lipophilic sunscreens that are active in the UVA and/or UVB range (absorbers) other than the two screening agents indicated. These additional screening agents can be selected, in particular, from among cinnamic derivatives; salicylic derivatives; camphor derivatives; triazine derivatives such as those described in EP-863,145, EP-517,104, EP-570,838, EP-796,851, EP-775,698 and EP-878,469; benzophenone derivatives; dibenzoylmethane derivatives; β,β'-diphenylacrylate derivatives, benzimidazole derivatives; p-aminobenzoic acid derivatives; screening polymers and screening silicones such as those described in WO-93/04665.

Exemplary additional sunscreens that are active in the UV-A and/or UV-B range include:
p-aminobenzoic acid,
oxyethylenated p-aminobenzoate (25 mol),
2-ethylhexyl p-dimethylaminobenzoate,
N-oxypropylenated ethyl p-aminobenzoate,
glyceryl p-aminobenzoate,
homomenthyl salicylate,
2-ethylhexyl salicylate,
triethanolamine salicylate,
4-isopropylbenzyl salicylate,
4-tert-butyl-4'-methoxydibenzoylmethane, Compound 32

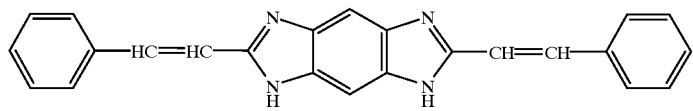

Compound 33

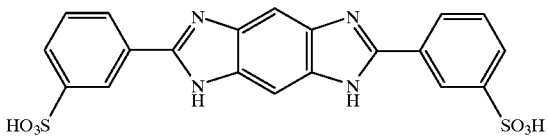

Compound 34

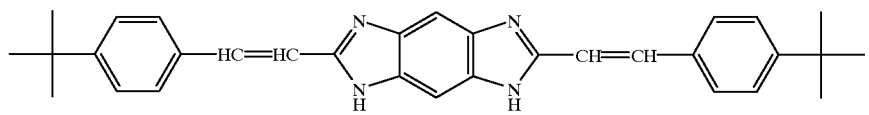

4-isopropyldibenzoylmethane,
2-ethylhexyl4-methoxycinnamate,
methyl diisopropylcinnamate,
isoamyl4-methoxycinnamate,
diethanolamine 4-methoxycinnamate,
menthyl anthranilate,
2-ethylhexyl 2-cyano-3,3'-diphenylacrylate,
ethyl 2-cyano-3,3'-diphenylacrylate,
2-phenyl-5-benzimidazolesulfonic acid and salts thereof,
3-(4'-trimethylammonio)benzylidenebornan-2-one methyl sulfate,
2-hydroxy-4-methoxybenzophenone,
2-hydroxy-4-methoxybenzophenone 5-sulfonate,
2,4-dihydroxybenzophenone,
2,2',4,4'-tetrahydroxybenzophenone,
2,2'-dihydroxy-4,4'-dimethoxybenzophenone,
2-hydroxy-4-n-octoxybenzophenone,
2-hydroxy-4-methoxy-4'-methylbenzophenone,
α-(2-oxoborn-3-ylidene)tolyl-4-sulfonic acid and salts thereof,
3-(4'-sulfo)benzylidenebornan-2-one and salts thereof,
3-(4'-methylbenzylidene)-d,1-camphor,
3-benzylidene-d,1-camphor,
benzene-1,4-bis(3-methylidene-10-camphorsulfonic acid) and salts thereof, urocanic acid,
2,4,6-tris[p-(2'-ethylhexyl-1'-oxycarbonyl)anilino]-1,3,5-triazine,
2-[(p-tert-butylamido)anilino]-4,6-bis[(p-2'-ethylhexyl-1'-oxycarbonyl)anilino]-1,3,5-triazine,
2,4-bis{[4-(2-ethylhexyloxy)-2-hydroxy]phenyl}-6-(4-methoxyphenyl)-1,3,5-triazine,
N-(2 and 4)-[(2-oxoborn-3-ylidene)methyl]benzyl]-acrylamide polymer, polyorganosiloxanes containing a malonate function.

The compositions according to the invention can also contain agents for artificially tanning and/or browning the skin (self-tanning agents) such as, for example, dihydroxyacetone (DHA).

The cosmetic compositions according to the invention can also contain pigments or nanopigments (average size of the primary particles: generally ranging from 5 nm to 100 nm, preferably from 10 nm to 50 nm) of coated or uncoated metal oxides such as, for example, nanopigments of titanium dioxide (amorphous or crystallized in rutile and/or anatase form), of iron oxide, of zinc oxide, of zirconium oxide or of cerium oxide, which are all UV photoprotective agents that are well known per se. Conventional coating agents include, moreover, alumina and/or aluminum stearate. Such coated or uncoated metal oxide nanopigments are described, in particular, in EP-A-0,518,772 and EP-A-0,518,773.

The compositions of the invention can also comprise conventional cosmetic additives and adjuvants selected, in particular, from among fatty substances, organic solvents, thickeners, softeners, antioxidants, opacifiers, stabilizers, emollients, hydroxy acids, antifoaming agents, moisturizers, vitamins, fragrances, preservatives, surfactants, fillers, sequestering agents, polymers, propellants, acidifying or basifying agents, dyes, colorants, or any other ingredients usually formulated into cosmetics, in particular for producing sunscreen/antisun compositions in the form of emulsions.

The fatty substances can be an oil or a wax or mixtures thereof, and they also comprise fatty acids, fatty alcohols and fatty acid esters. The oils can be selected from among animal oils, plant oils, mineral oils or synthetic oils and, in particular, include liquid petroleum jelly, liquid paraffin, volatile or nonvolatile silicone oils, isoparaffins, poly-α-olefins, fluoro oils and perfluoro oils. Similarly, the waxes are advantageously animal waxes, fossil waxes, plant waxes, mineral waxes or synthetic waxes that per se known to this art.

Exemplary organic solvents include the lower alcohols and polyols.

The thickeners are selected, in particular, from among crosslinked acrylic acid homopolymers, and modified or unmodified guar gums and celluloses, such as hydroxypropyl guar gum, methylhydroxyethylcellulose, hydroxypropylmethylcellulose or hydroxyethylcellulose.

One skilled in this art will take care to select this or these optional additional compound(s) and/or the amounts thereof such that the advantageous properties, in particular the level of photoprotection, intrinsically associated with the binary combination in accordance with the invention are not, or are not substantially, adversely affected by the additions envisaged.

The compositions of the invention can be formulated according to the techniques that are well known to this art, in particular for the preparation of emulsions of oil-in-water or water-in-oil type.

This compositions can be, in particular, in the form of a simple or complex emulsion (O/W, W/O, O/W/0 or W/O/W emulsion) such as a cream, a milk, a gel or a cream-gel, a lotion, a powder or a solid tube and can optionally be packaged as an aerosol and can be in the form of a mousse or spray.

When an emulsion, the aqueous phase of this emulsion can comprise a nonionic vesicular dispersion prepared according to known processes (Bangham, Standish and Watkins. *J. Mol. Biol.*, 13, 238 (1965), FR-2,315,991 and FR-2,416,008).

The cosmetic compositions of the invention are well suited for protecting the human epidermis or the hair against ultraviolet rays, as an antisun composition or as a makeup product.

When the cosmetic composition according to the invention is formulated for protecting the human epidermis against UV rays, or as an antisun composition, it can be in the form of a suspension or a dispersion in solvents or fatty substances, in the form of a nonionic vesicular dispersion, or in the form of an emulsion, preferably of oil-in-water type, such as a cream or a milk, in the form of an ointment, a gel, a cream-gel, a powder, a solid tube, a stick, an aerosol mousse or a spray.

When the cosmetic composition according to the invention is formulated for protecting the hair, it can be in the form of a shampoo, a lotion, a gel, an emulsion or a nonionic vesicular dispersion and can constitute, for example, a rinse-out composition, to be applied before or after shampooing, before or after dyeing or bleaching, before, during or after permanent-waving or straightening the hair, a styling or treating lotion or gel, a blow-drying or hairsetting lotion or gel, or a composition for permanent-waving, straightening, dyeing or bleaching the hair.

When the composition is formulated as a makeup product for the eyelashes, the eyebrows or the skin, such as an epidermal treatment cream, a foundation, a tube of lipstick, an eyeshadow, a face powder, a mascara or an eyeliner, it can be in solid or pasty, anhydrous or aqueous form, such as oil-in-water or water-in-oil emulsions, nonionic vesicular dispersions or suspensions.

For example, for the antisun formulations in accordance with the invention which comprise a support of oil-in-water emulsion type, the aqueous phase (in particular comprising the hydrophilic screening agents) advantageously constitutes from 50% to 95% by weight, preferably from 70% to 90% by weight, relative to the total weight of the formulation, the oily phase (in particular comprising the lipophilic screening agents) advantageously constitutes from 5% to 50% by weight, preferably from 10% to 30% by weight, relative to the total weight of the formulation, and the (co)-emulsifier(s) represents) from 0.5% to 20% by weight, preferably from 2% to 10% by weight, relative to the total weight of the formulation.

As indicated above, the present invention also features a cosmetic treatment regime/regimen for the skin or the hair which is intended to protect same against the deleterious effects of UV radiation and which entails topically applying an effective amount of a subject cosmetic composition onto the skin or the hair.

In order to further illustrate the present invention and the advantages thereof, the following specific example is given, it being understood that same is intended only as illustrative and in nowise limitative.

EXAMPLE

| COMPOSITION | Amount |
| --- | --- |
| 80/20 mixture of cetylstearyl alcohol and of oxyethylenated (33 EO) cetylstearyl alcohol (Sinnowax AO - Henkel) | 7 g |
| Mixture of glyceryl mono- and distearate (Cerasynt SD-V ISP) | 2 g |
| Cetyl alcohol | 1.5 g |
| Polydimethylsiloxane (Dow Corning 200 Fluid - Dow Corning) | 1 g |
| $C_{12}/C_{15}$ alkyl benzoate (Witconol TN - Witco) | 15 g |
| Glycerol | 20 g |
| Sodium salt of 1,4-bis(benzimidazolyl)phenylene-3,3',5,5'-tetrasulfonic acid (Compound 4) | 3 g |
| 2,2'-Methylenebis[6-(2H-benzotriazol-2-yl)-4-(1,1,3,3-tetramethylbutyl)phenol] (Compound (a)) marketed under the trademark Mixxim BB/100 by Fairmont Chemical | 5 g |
| Triethanolamine | qs pH 7 |
| Preservatives | qs |
| Demineralized water       qs | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the photoprotection of human skin and/or hair, comprising SPF synergistically UV-photoprotecting effective amounts of each of (a) at least one bis-hydroxyphenylbenzotriazole sunscreen compound and (b) at least one second sunscreen compound which comprises at least two benzazolyl functional groups and/or at least one sunscreen compound which comprises at least one benzodiazolyl functional group, formulated into a topically applicable, cosmetically acceptable vehicle, diluent or carrier therefor.

2. The sunscreen/cosmetic composition as defined by claim 1, said at least one bis-hydroxyphenylbenzotriazole compound (a) having the structural formula (I):

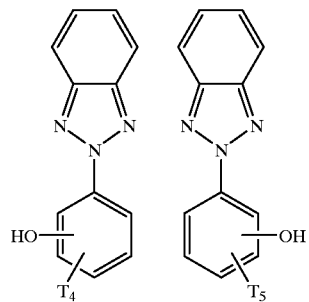

(I)

in which the radicals $T_4$ and $T_5$, which may be identical or different, are each a $C_1$–$C_{18}$ alkyl radical optionally substituted with one or more $C_1$–$C_4$ alkyl, $C_5$–$C_{12}$ cycloalkyl and/or aryl radicals.

3. The sunscreen/cosmetic composition as defined by claim 2, wherein formula (I), $T_4$ and $T_5$ are simultaneously each a α,α-dimethylbenzyl radical.

4. The sunscreen/cosmetic composition as defined by claim 1, said at least one bis-hydroxyphenylbenzotriazole compound (a) having the structural formula (II):

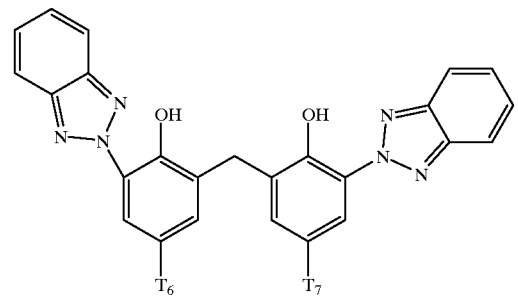

(II)

in which the radicals $T_6$ and $T_7$, which may be identical or different, are each a $C_1$–$C_{18}$ alkyl radical optionally substituted with one or more $C_1$–$C_4$ alkyl, $C_5$–$C_{12}$ cycloalkyl and/or aryl radicals.

5. The sunscreen/cosmetic composition as defined by claim 4, said at least one compound of formula (II) being:

Compound (a)

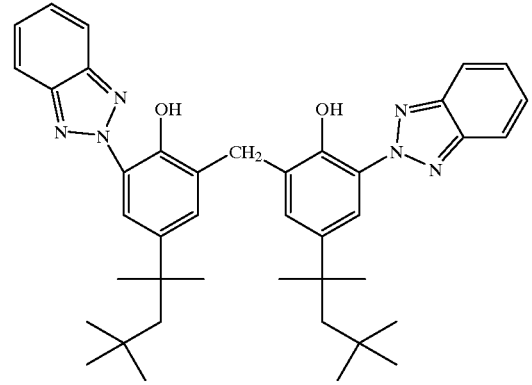

or

Compound (b)

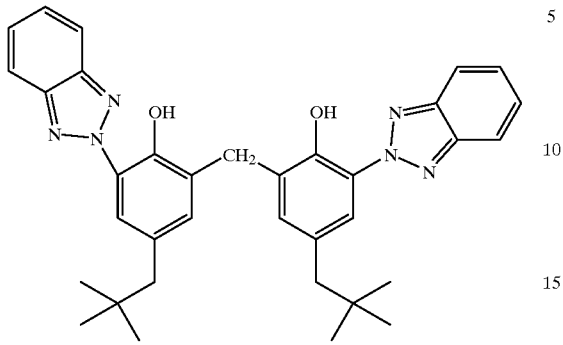

6. The sunscreen/cosmetic composition as defined by claim 1, said at least one bis-hydroxyphenylbenzotriazole compound (a) comprising from about 0.1% to 15% by weight thereof.

7. The sunscreen/cosmetic composition as defined by claim 6, said at least one bis-hydroxyphenylbenzotriazole compound (a) comprising from about 0.2% to 10% by weight thereof.

8. The sunscreen/cosmetic composition as defined by claim 1, said at least one bis-hydroxyphenylbenzotriazole compound (a) comprising insoluble particulates thereof.

9. The sunscreen/cosmetic composition as defined by claim 8, said at least one bis-hydroxyphenylbenzotriazole compound (a) comprising insoluble micronized particles.

10. The sunscreen/cosmetic composition as defined by claim 9, said at least one bis-hydroxyphenylbenzotriazole compound (a) comprising insoluble micronized particles having an average particle size ranging from 0.01 to 2 $\mu$m.

11. The sunscreen/cosmetic composition as defined by claim 10, said at least one bis-hydroxyphenylbenzotriazole compound (a) comprising insoluble micronized particles having an average particle size ranging from 0.02 to 1.5 $\mu$m.

12. The sunscreen/cosmetic composition as defined by claim 11, said at least one bis-hydroxyphenylbenzotriazole compound comprising insoluble micronized particles having an average particle size ranging from 0.05 to 1.0 $\mu$m.

13. The sunscreen/cosmetic composition as defined by claim 9, said insoluble micronized particles having been produced by grinding course particles of said at least one bis-hydroxyphenylbenzotriazole compound in the presence of a surfactant.

14. The sunscreen/cosmetic composition as defined by claim 13, said surfactant comprising an alkylpolyglucoside of structure $C_nH_{2n+1}O(C_6H_{10}O_5)_xH$ in which n is an integer ranging from 8 to 16 and x is the average degree of polymerization of the structural unit $(C_6H_{10}O_5)$ and ranges from 1.4 to 1.6.

15. The sunscreen/cosmetic composition as defined by claim 14, said alkylpolyglucoside surfactant having been prepared by reacting a $C_1$–$C_{12}$ carboxylic acid with one or more free OH functions on the glucoside unit $(C_6H_{10}O_5)$.

16. The sunscreen/cosmetic composition as defined by claim 15, said $C_1$–$C_{12}$ carboxylic acid comprising formic acid, acetic acid, propionic acid, butyric acid, sulfosuccinic acid, tartaric acid or citric acid.

17. The sunscreen/cosmetic composition as defined by claim 13, comprising grinding in the presence of a surfactant, said surfactant being at a concentration ranging from 1% to 50% by weight relative to the bis-hydroxyphenylbenzotriazole compound (a) in its micronized form.

18. The sunscreen/cosmetic composition as defined by claim 1, comprising at least one sunscreen compound (b) which comprises at least two benzazolyl functional groups and having the structural formula (III):

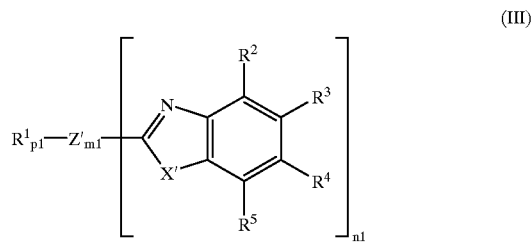

in which Z' is an organic residue of valency $(p_1+n_1)$ comprising one or more double bonds situated such that they complete the system of double bonds of at least two benzazolyl functional groups, which may be identical or different, as circumscribed within the brackets to constitute a totally conjugated moiety; X' is S, O or $NR^6$ ; $R^1$ is hydrogen, $C_1$–$C_{18}$ alkyl, $C_1$–$C_4$ alkoxy, $C_5$–$C_{15}$ aryl, $C_2$–$C_{18}$ acyloxy, $SO_3Y'$ or COOY'; the radicals $R^2$, $R^3$, $R^4$ and $R^5$, which may be identical or different, are each a nitro group or a radical $R^1$; $R^6$ is hydrogen, $C_1$–$C_4$ alkyl or $C_1$–$C_4$ hydroxyalkyl; Y' is hydrogen, Li, Na, K, $NH_4$, 1/2Ca, 1/2Mg, 1/3Al or a cation resulting from the neutralization of a free acid group with a nitrogenous organic base; m, is 0 or 1; $n_1$ is a number ranging from 2 to 6; and $p_1$ is a number ranging from 1 to 4; with the proviso that $p_1+n_1$ does not exceed the value 6.

19. The sunscreen/cosmetic composition as defined by claim 18, wherein formula (III), the radical Z' is selected from among:

(a) an olefinic linear aliphatic $C_2$–$C_6$ hydrocarbon-based radical which can be interrupted with a $C_5$–$C_{12}$ aryl group or a $C_4$–$C_{10}$ heteroaryl group;

(b) a $C_5$–$C_{15}$ aryl radical which can be interrupted with an olefinic linear aliphatic $C_2$–$C_6$ hydrocarbon-based radical;

(c) a $C_3$–$C_{10}$ heteroaryl radical; with the provisio that said radical Z' is optionally substituted with $C_1$–$C_6$ alkyl, $C_1$–$C_6$ alkoxy, phenoxy, hydroxyl, methylenedioxy or amino radicals, themselves optionally substituted with one or two $C_1$–$C_5$ alkyl radicals.

20. The sunscreen/cosmetic composition as defined by claim 18, wherein formula (III), the radical Z' is selected from among:

—CH=CH—

—CH=CH—CH=CH—

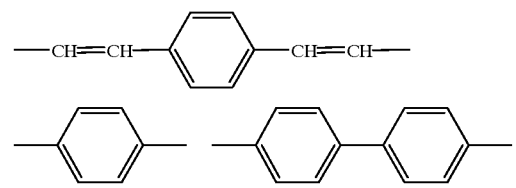

-continued
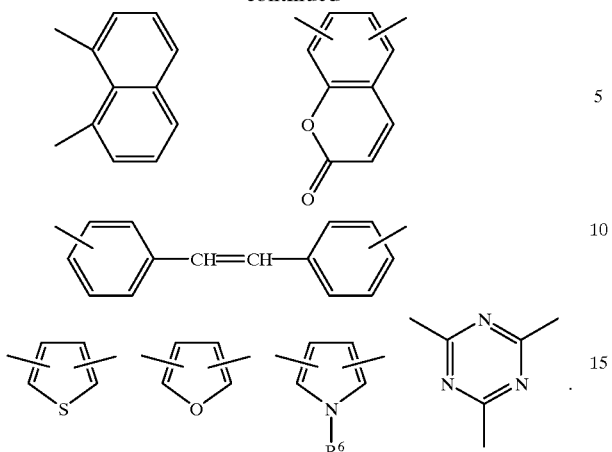
21. The sunscreen/cosmetic composition as defined by claim 18, said at least one compound of formula (III) being selected from among the following compounds, or one of the salts thereof:
Compound 1
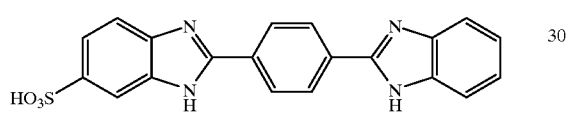
Compound 2
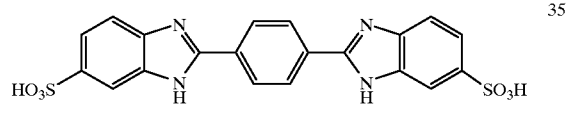
Compound 3
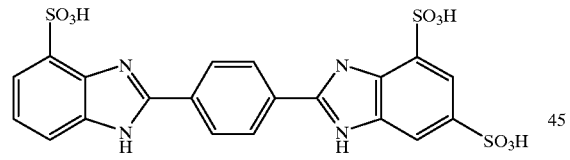
Compound 4
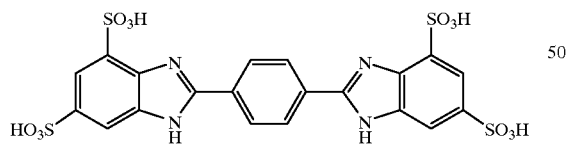
Compound 5
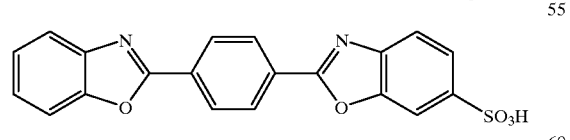
Compound 6
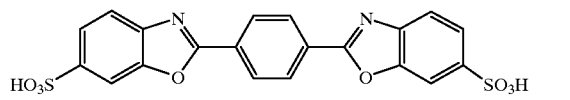
Compound 7
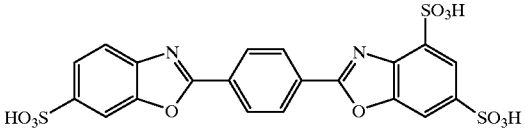
Compound 8
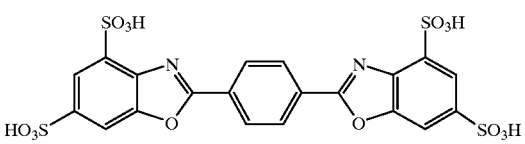
Compound 9
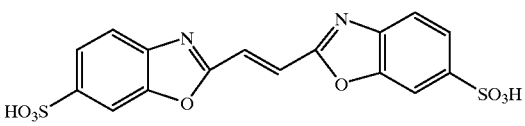
Compound 10
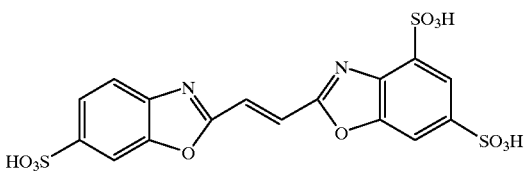
Compound 11
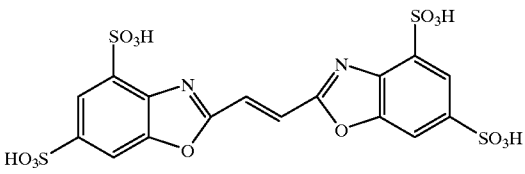
Compound 12
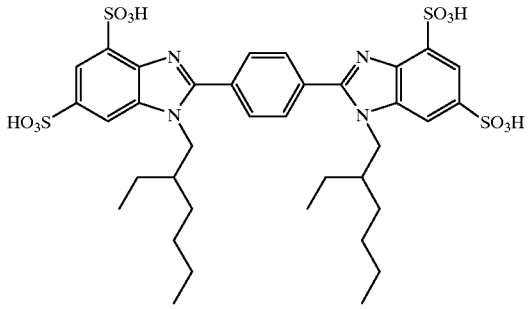
Compound 13
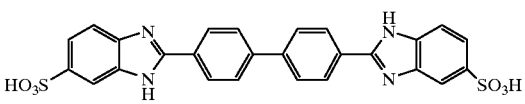

Compound 14
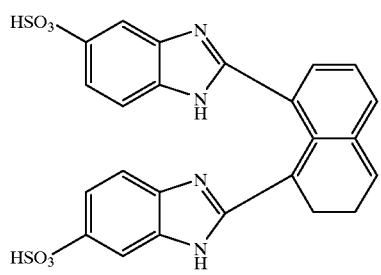
Compound 15
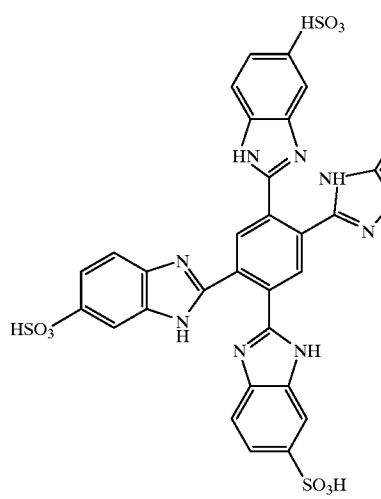
Compound 16
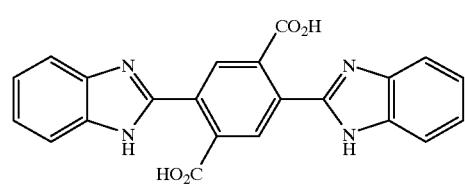
Compound 17
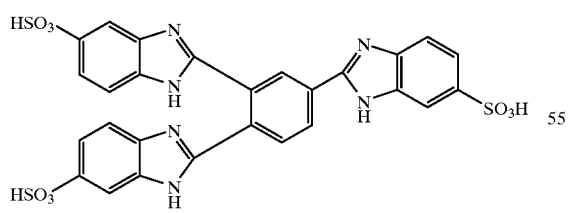
Compound 18
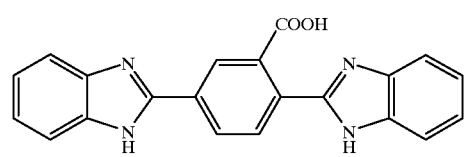
Compound 19
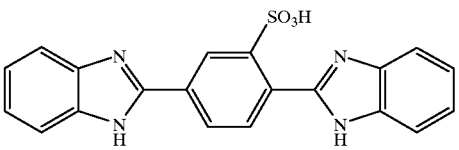
Compound 20
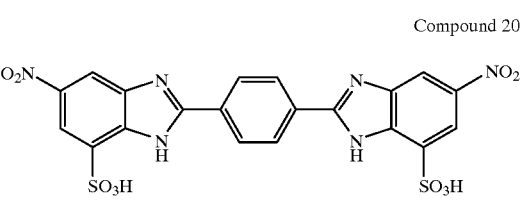
Compound 21
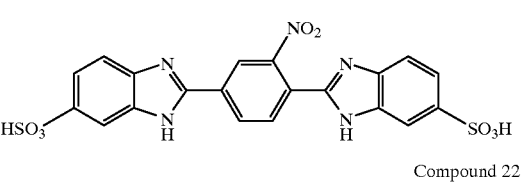
Compound 22
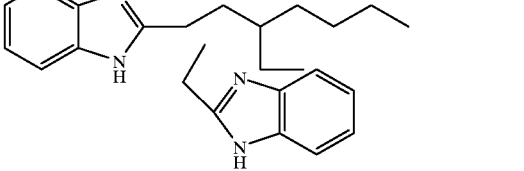
Compound 23
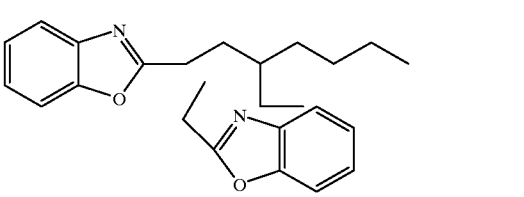
Compound 24
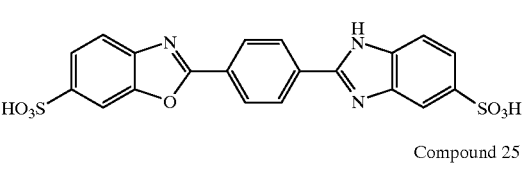
Compound 25
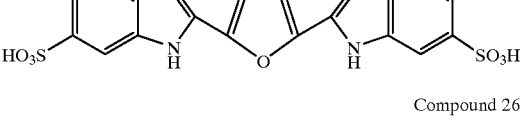
Compound 26
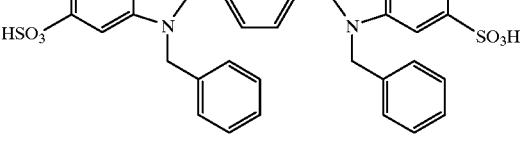

Compound 27

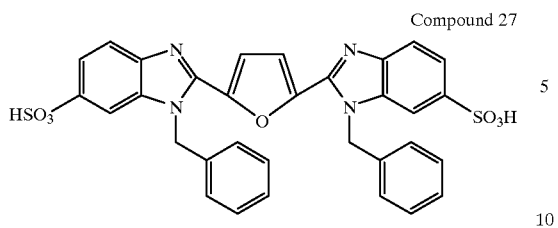

Compound 29

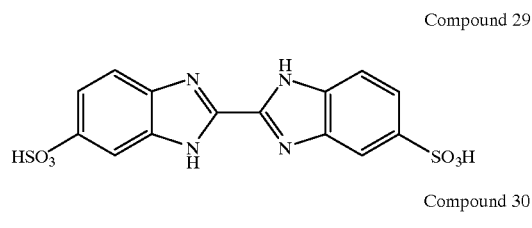

Compound 30

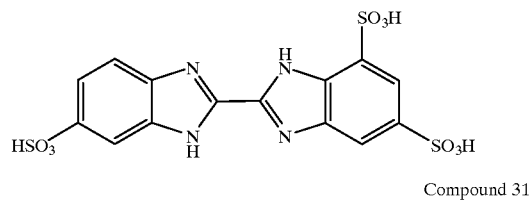

Compound 31

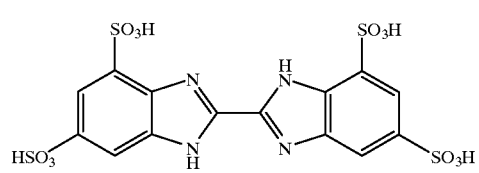

22. The sunscreen/cosmetic composition as defined by claim 21, said at least one compound of formula (III) comprising 1,4-bis(benzimidazolyl)phenylene-3,3',5,5'-tetrasulfonic acid (Compound 4), or salt thereof, having the following structure:

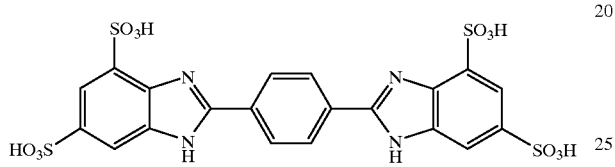

23. The sunscreen/cosmetic composition as defined by claim 1, comprising at least one sunscreen compound (b) which comprises at least two benzazolyl functional groups and being selected from among the following compounds, or one of the salts thereof:

24. The sunscreen/cosmetic composition as defined by claim 1, comprising at least one sunscreen compound (b) which comprises at least one benzodiazolyl functional group and being selected from among the following compounds, or one of the salts thereof:

Compound 32

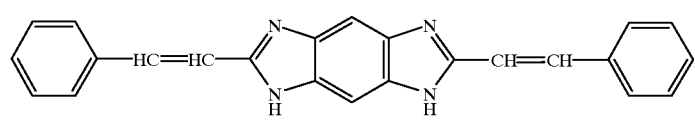

Compound 33

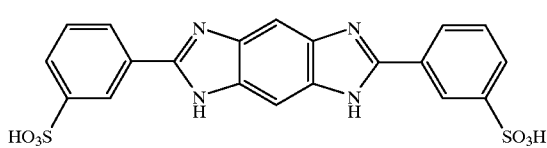

Compound 34

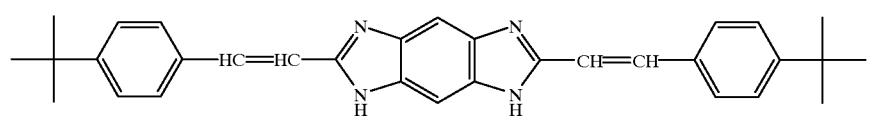

25. The sunscreen/cosmetic composition as defined by claim 1, said at least one sunscreen compound (b) which comprises benzazolyl and/or benzodiazolyl functional groups comprising from 0.1% to 15% by weight thereof.

26. The sunscreen/cosmetic composition as defined by claim 25, said at least one sunscreen compound (b) comprising from 0.2% to 10% by weight thereof.

27. The sunscreen/cosmetic composition as defined by claim 1, formulated as an oil-in-water emulsion.

28. The sunscreen/cosmetic composition as defined by claim 1, further comprising at least one additional hydro- Compound 28

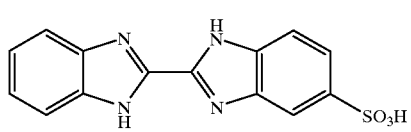

philic or lipophilic organic UV-A and/or UV-B sunscreen other than said first and second sunscreens (a) and (b).

29. The sunscreen/cosmetic composition as defined by claim 28, further comprising at least one cinnamic derivative, salicylic derivative, camphor derivative, triazine derivative, benzimidazole derivative, dibenzoylmethane derivative, benzimidazole derivative, β-β-diphenylacrylate derivative, p-aminobenzoic acid derivative, sunscreen polymer, or sunscreen silicone.

30. The sunscreen/cosmetic composition as defined by claim 1, further comprising a photoprotecting effective amount of particulates of at least one coated or uncoated inorganic pigment or nanopigment.

31. The sunscreen/cosmetic composition as defined by claim 30, said at least one pigment or nanopigment comprising titanium oxide, zinc oxide, iron oxide, zirconium oxide, cerium oxide or mixture thereof.

32. The sunscreen/cosmetic composition as defined by claim 1, further comprising at least one active agent for artificially tanning and/or browning of human skin.

33. The sunscreen/cosmetic composition as defined by claim 1, further comprising at least one cosmetically acceptable adjuvant or additive.

34. The sunscreen/cosmetic composition as defined by claim 33, said at least one adjuvant or additive comprising a fat, organic solvent, thickening agent, softener, antioxidant, opacifying agent, stabilizing agent, emollient, hydroxy acid, anti-foaming agent, moisturizer, vitamin, fragrance preservative, surfactant, filler, sequestering agent, polymer, propellant, basifying or acidifying agent, dye, colorant, or mixture thereof.

35. The sunscreen/cosmetic composition as defined by claim 1, comprising a nonionic vesicle dispersion, emulsion, cream, milk, gel, cream gel, suspension, dispersion, powder, solid stick or tube, foam or spray.

36. The sunscreen/cosmetic composition as defined by claim 1, comprising a makeup.

37. The sunscreen/cosmetic composition as defined by claim 36, comprising an anhydrous or aqueous solid or paste, emulsion, suspension, or dispersion.

38. The sunscreen/cosmetic composition as defined by claim 1, comprising a shampoo, lotion, gel, nonionic vesicular dispersion, or rinse.

39. The sunscreen/cosmetic composition as defined by claim 1, having a sun protection factor of at least 2.

40. A regime/regimen for protecting human skin and/or hair against the deleterious effects of ultraviolet irradiation, comprising topically applying thereto an effective UV-photoprotecting amount of the sunscreen/cosmetic composition as defined by claim 1.

41. A regime/regimen for protecting human skin and/or hair against the deleterious effects of solar radiation, comprising topically applying thereto an effective UV-photoprotecting amount of the sunscreen/cosmetic composition as defined by claim 1.

* * * * *